（12） United States Patent
Corson et al.

(10) Patent No.: US 7,089,123 B2
(45) Date of Patent: Aug. 8, 2006

(54) ARRAY SCANNER CONTROL SYSTEM

(75) Inventors: John F. Corson, Mountain View, CA (US); Andreas N. Dorsel, Menlo Park, CA (US)

(73) Assignee: Agilent Technologies, Inc, Palo Alto, CA (US)

( * ) Notice: Subject to any disclaimer, the term of this patent is extended or adjusted under 35 U.S.C. 154(b) by 333 days.

(21) Appl. No.: 10/261,563

(22) Filed: Sep. 30, 2002

(65) Prior Publication Data

US 2004/0064264 A1 Apr. 1, 2004

(51) Int. Cl.
*G01N 33/48* (2006.01)

(52) U.S. Cl. ............... 702/31; 702/18; 702/27; 250/208.1; 250/252.1; 250/458.1; 250/459.1; 250/461.1

(58) Field of Classification Search ............ 702/19, 702/27, 31; 713/200; 250/208.1, 252.1, 458.1, 250/459.1, 461.2; 348/229.1; 356/230, 318; 358/406
See application file for complete search history.

(56) References Cited

U.S. PATENT DOCUMENTS

| 5,091,652 | A | 2/1992 | Mathies et al. |
| 5,260,578 | A | 11/1993 | Bliton et al. |
| 5,296,700 | A | 3/1994 | Kumagai |
| 5,324,633 | A | 6/1994 | Fodor et al. |
| 5,585,639 | A | 12/1996 | Dorsel et al. |
| 5,760,951 | A | 6/1998 | Dixon et al. |
| 5,763,870 | A | 6/1998 | Sadlere et al. |
| 6,078,390 | A | 6/2000 | Bengtsson |
| 6,084,991 | A | 7/2000 | Sampas |
| 6,215,894 | B1 * | 4/2001 | Zeleny et al. ............... 382/133 |
| 6,222,664 | B1 | 4/2001 | Dorsel |
| 6,284,465 | B1 | 9/2001 | Wolber |
| 6,320,196 | B1 | 11/2001 | Dorsel et al. |
| 6,371,370 | B1 | 4/2002 | Sadler et al. |
| 6,406,849 | B1 | 6/2002 | Dorsel et al. |
| 6,471,916 | B1 * | 10/2002 | Noblett ................. 422/82.08 |

OTHER PUBLICATIONS

Agilent G2565AA "Microarray Scnner System with SureScan Technology" UserM anuel, Agilent Technologies,M ay 2002.

* cited by examiner

*Primary Examiner*—Michael Nghiem
*Assistant Examiner*—Stephen J. Cherry

(57) ABSTRACT

An optical scanning system adapted to physically adjust scanner settings in response to control feature readings is disclosed. The scanner and methodology finds particular use in reading of biopolymer arrays. The system may operate in any of a number of ways such that optimal data from scans is obtained. It may also be possible to use the system as a tool to aid in manufacture of arrays by providing feedback to a manufacturer regarding the signal produce for a given batch of samples tested.

14 Claims, 9 Drawing Sheets

ARRAY SCANNER CONTROL SYSTEM

FIELD OF THE INVENTION

This invention relates to optical scanners and, more particularly, optimally setting systems for multi-channel scanning.

BACKGROUND OF THE INVENTION

Optical scanners find use in performing detection for various experiments, assays and the like. They are often used in array analysis systems for detection of surface bound binding complexes in genomic and proteomic applications, often in connection with microarray devices.

Array use sometimes involves "target" spots of DNA (or RNA) bound to a substrate. Each spot, or sample, of DNA constitutes a separate experiment. To conduct an experiment, "Probe" DNA or RNA which has been labeled with a fluorophor is then introduced to the surface of the slide and is allowed to hybridize with the target DNA. Suitable fluorophores including fluorescein, lissamine, phycoerythrin, rhodamine (Perkin Elmer Cetus), Cy2, Cy3 (green), Cy3.5, Cy5 (red), Cy5.5, Cy7, FluorX (Amersham) and others, as are well known (see Kricka, 1992, Nonisotopic DNA Probe Techniques, Academic Press San Diego, Calif.). Excess probe DNA that does not bind with target DNA is removed from the surface of the slide in a subsequent washing process.

Such an experiment allows the binding affinity between the probe and target DNA to be measured to determine the likeness of their molecular structures; complementary molecules have a much greater probability of binding than unrelated molecules. The probe DNA is labeled with fluorescent labels that emit a range of radiation energy centered about and including a certain wavelength when excited by an external radiation source of a shorter wavelength. The brightness of emitted radiation is a function of the fluor density in the illuminated sample. Because the fluor density is a function of the binding affinity or likeness of the probe molecule to the target molecule, the brightness of each sample can be mapped as to the degree of similarity between the probe DNA and the target DNA present. On a typical microarray, up to tens of thousands of experiments can be performed simultaneously on the probe DNA, allowing for a detailed characterization of complex molecules.

An optical scanner is used to retrieve such data as is available. Generally, fluorescence-based micro-array scanners incorporate the ability to deliver multiple laser excitation wavelengths so that fluorescence data can be obtained from the sample at two or more emission wavelengths by detecting two or more fluorescent dyes. Many DNA microarrays are utilized in connection with a two-wavelength scanning method, where the results of one wavelength scan are used as control values and the results of the other wavelength scan represent the desired experimental result. Such an approach is employed in Differential Gene Expression assays.

Typically, pairs (or increasing numbers) of fluorophores are chosen that have distinct emission spectra so that they can be easily distinguished by the scanner. However, as the market and applications mature, and a larger variety of suitable dyes become available, the demand for alternative excitation wavelengths and emission bands will increase. U.S. Pat. No. 6,355,934 is directed to systems suited to accommodate such future needs, thereby providing background for potential applications of the present invention.

Whatever the case, the present invention involves approaches for achieving full data acquisition. In order to properly interpret data obtained from a plurality of scanned channels, it has been appreciated that the intensity of the recorded signal for the different channels should be averaged or normalized. Otherwise, as in Differential Gene Expression tests, sample data and control data will be skewed relative to each other. It has been appreciated that system asymmetries can produce unbalanced results between channels that should otherwise produce an equivalent intensity based on some metric.

To account for this, a number of approaches have been developed by which normalization or channel balance may be attempted. One approach described in the aforementioned U.S. Pat. No. 6,351,712 is to set average signal intensity for the scanned channels to an equivalent value after the data has been obtained, thereby scaling the other results obtained. Another procedure described therein involves normalization between channels using the intensity ratio of genomic DNA spots.

U.S. Pat. No. 6,344,316 describes another software or post-data acquisition processing approach. Here, a system is described in which the signal intensities obtained from scanning oligonucleotide control probes that are perfectly complementary to a labeled reference are used as a mathematical devisor for feature intensity readings taken by each corresponding channel.

In contrast, U.S. Pat. No. 6,078,390 describes a system which operates by performing a partial scan and then adjusting each channel so that the brightest detected features are, on average, set to a predetermined maximum unsaturated value. This system implicitly relies on the assumption that a full scan of an array will yield results consistent with the partial scan results.

Each of these approaches has its drawbacks. The image post-processing techniques involving software manipulation of data that can result in loss or clipping of high-end or low-end data which is not acquired due to setup inadequacy (i.e., non-optimal detector gain or excitation source power settings). The system described in the '390 patent also relies on assumptions that may result in failure to acquire what data is available. Furthermore, by balancing channels in view of the most intense readings obtained, the likelihood of error is increased since maximum intensity features will generally be the least common signal received.

Another disadvantage of what is taught by the '390 patent is that the brightest red and green features will not necessarily have a known ratio. When running an experiment with a two-color array, the differential expression of the sample on various probe features is what is being measured. Therefore, the brightest features of red and green may not have a ratio equal to or substantially equal to 1 even while the ratio of the average red and average green features is equal to 1. As such, the channels may actually be set out of balance by the regime taught in that patent. This will skew scanner results rather than appropriately normalize them.

Accordingly, there exists a need for a scanner system more closely tied to the details and/or realities of data acquisition in which potential data is not lost, and in which reliable data—not merely prospectively representative data—is used to balance or equalize the experimental channels using adjustments in the scanner. The present invention meets this need. Other needs and advantages presented by the present invention may also be apparent to those with skill in the art upon review of the following disclosure.

SUMMARY OF THE INVENTION

According to the present invention, control features are provided in connection with an array. Upon scanning these features (alone or in connection with scanning an entire array, including target or test features), if their expected intensities do not correspond substantially to a desired or expected ratio (generally 1:1), scanner system parameters are adjusted to run a subsequent scan of the control features alone or of the entire array.

Recalibration of the scanner settings based on the data obtained by scanning the control features allows for setting scanner sensitivity to the correct ratios and for maximum data retrieval from a subsequent scan. While a second scan of an entire array provided in such fashion may result in undesirably photobleaching, accepting or accounting for this effect in the present invention is preferable to potentially failing to scan for data at the limits of detection by merely employing image processing to obtain normalized results.

Also, the present invention contemplates the use of the color-control features in determining scanner channel settings. Another option is to determine scanner setting first based on all the test features of the array and then apply correction factor(s) determined in view of the control feature intensity. Measurement of scan channel controls may also be utilized for the purpose of providing correction factors to a plurality of subsequent array scans setup, e.g., for maximum sensitivity and to produce non-saturated results, respectively. Still further, control feature readings may be employed to adjust systems settings to account for non-linearities present in the dyes used for each channel which is scanned. Yet another aspect of the invention involves using a system that has been properly calibrated to quality control or test arrays produced by manufactures that are attempting to provide arrays with consistent control features.

The present invention includes the subject methodology, programming defining the same, hardware configured to run according to the methodology and results or data produced according to the teachings of the present invention.

DEFINITIONS

Figure 1:
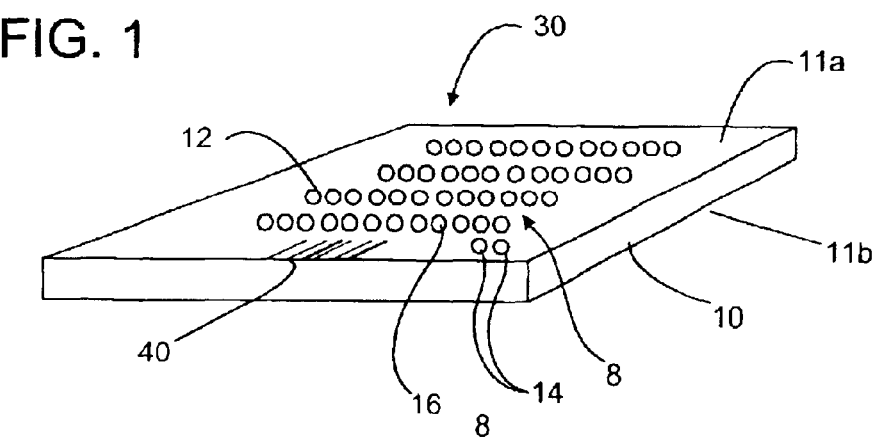
FIG. 1 is a perspective view of an array package including a substrate carrying a typical array, as may be used in the present invention.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer/polymer) of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," includes any two-dimensional or substantially two-dimensional (as well as a three-dimensional) arrangement of addressable regions bearing a particular chemical moiety or moieties (e.g., biopolymers such as polynucleotide sequences (nucleic acids), polypeptides (e.g., proteins), etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc:

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

In describing the invention in greater detail than provided in the Summary above, suitable hardware for use in the invention is first described. This discussion is followed by description of the subject methods and array use.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events that is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless defined otherwise below, all technical and scientific terms used herein have the same meaning as commonly understood by one of ordinary skill in the art to which this invention belongs. Still, certain elements are defined herein for the sake of clarity.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Figure 2:
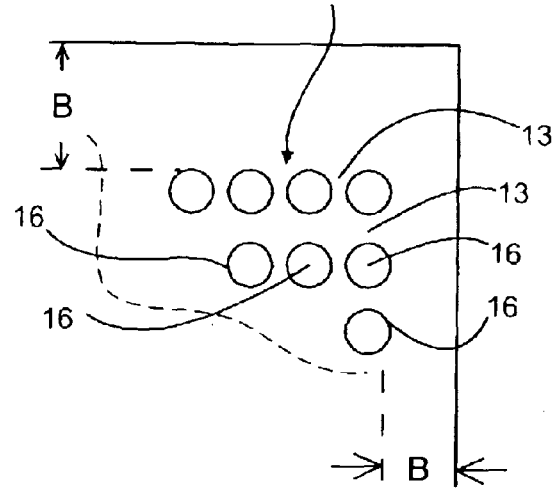
FIG. 2 is an enlarged view of a portion of FIG. 1 showing some of the identifiable individual regions of the array of FIG. 1.
Figure 3:
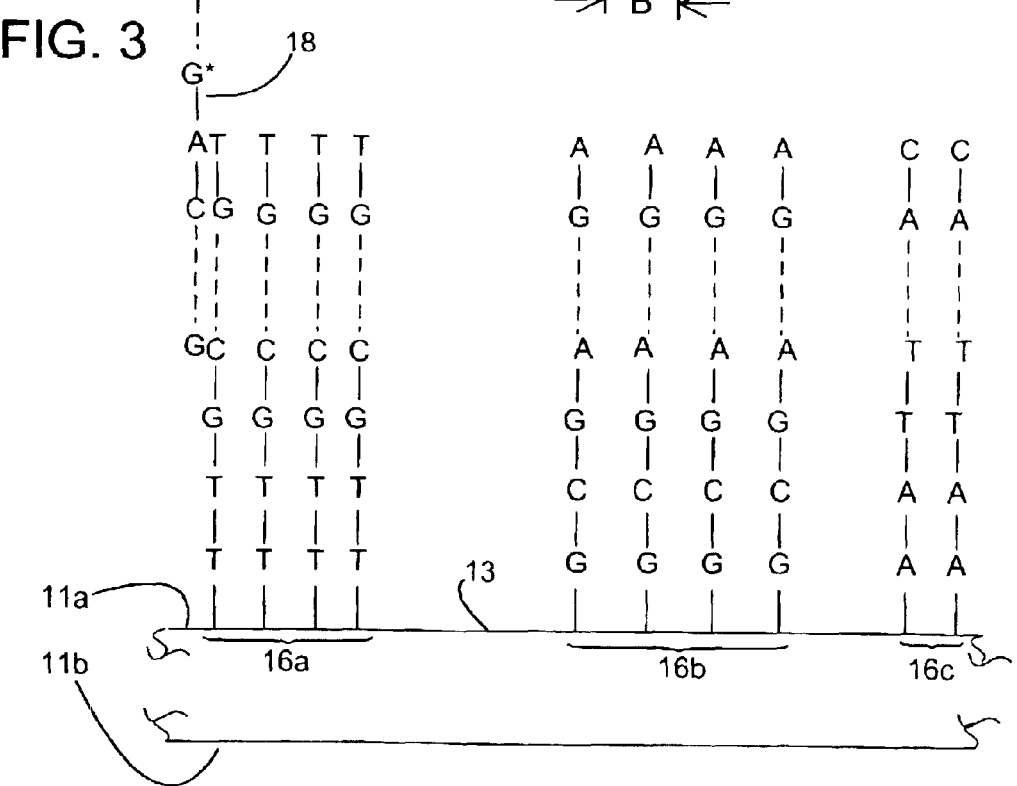
FIG. 3 is a grossly enlarged cross-section of a portion of FIG. 2.

By "saturated results" or "saturated features," what is meant the condition of a scanner channel topping-out or getting pegged at the upper end of its range (e.g., 65535 for a $2^{16}$-1 bit range) by a high signal. By "non-linear" or "non-linearity" what is meant that a given signal or process/activity departs from a proportional relationship between input and output. By "matching" or being the "same" what is mean is that there be substantial correspondence between compared values; the correspondence will generally be better than within about 5%, more preferably within about 2.5%, and most preferably within about 1% or better.
Hardware Turning now to the figures, FIGS. 1–3 show an array in the form of a contiguous, substantially planar substrate 10 that carries multiple probe features 16 disposed across a first surface 11a of substrate 10 separated by interfeature areas 13. The substrate is preferably made of transparent material to facilitate data acquisition scanning there through. Alternatively, the substrate could be scanned from the side that carries the array. Features 16 are shown disposed in a pattern that defines the array. The extent of the pattern defines the scan region 8. A second surface 11b of substrate 10 does not carry any features. Substrate 10 may be of any shape although the remainder of any package carrying substrate 10, and the apparatus of the present invention, may need to be adapted accordingly.

A typical array usually includes at least two distinct polymers that differ by monomeric sequence immobilized on (i.e., covalently or non-covalently attached to) different and known locations on the substrate surface, where a space between each location or feature may or may not be present. Each distinct polymeric sequence of the array is typically present as a composition of multiple copies of the polymer on the substrate surface (e.g. as a spot or feature 16 on the surface of the substrate). The number of distinct polymeric sequences, and hence probe features 16, present on the slide or substrate may vary, but is generally at least 10, where the number may be as high as at least 50, 100, 500, 1000 or 10,000. The density of features present on the array surface may vary, but will generally be at least about 10 and usually at least about 100 spots/cm$^2$, where the density may be as high as 10$^6$ or higher, but will generally not exceed about 10$^5$ spots/cm$^2$.

While all probe features 16 may be of different composition, some could be the same (e.g. when any repeats of each feature composition are excluded the remaining features may account for at least 5%, 10%, or 20% of the total number of features). In any event, each feature carries probes in the form of a one moiety or mixture of moieties, which in the case of each feature 16 in FIGS. 1–3 is preferably a polynucleotide having a particular sequence, while interfeature areas 13 do not carry any moieties of a type the same as the features 16 (i.e., no polynucleotides in the case of features 16 carrying polynucleotides).

Such an array configuration is illustrated schematically in FIG. 3 where regions 16 are shown as carrying different polynucleotide sequences. Probe features 16 may have widths (that is, diameter, for a round spot) of at least 5 or 10 μm, and usually less than 1.0 cm. In embodiments where very small spot sizes or feature sizes are desired, each of the features 16 may have widths of at least 1.0 μm and less than 1.0 mm, usually less than 500 μm, and more usually less than 200 μm. Features that are not round may have areas equivalent to the area ranges of round probe features 16 resulting from the foregoing diameter ranges. The probes of features 16 are typically linked to substrate 10 through a suitable linker (not shown).

Control features 14 provided on substrate 10 may be included together with the probe features, or in independent region(s) as shown in FIG. 1. The physical characteristics of the control features may be like those of the probe features, or otherwise. In any case, the control features are designed so that they will exhibit certain predetermined fluorescence intensity properties when scanned.

A first option is that a single control feature 14 be provided for each scanner channel. For example, a Cy3 and a Cy5 control feature may be provided. In which case, the set of features will be configured to present intensities at a known or expected ratio (usually 1:1) when the scanner system is configured properly, the array is printed correctly and the hybridization is done correctly. This may include control features that result in an absolute signal level. It is further contemplated that more than one controls feature be provided for each channel. In which case, the controls may be configured to result in different expected intensities when scanned.

A number of ways exist in which to produce control features having known or expected intensities (or ratios between those for different channels). These ways include synthetic attachment of a fluorophore, deposition of a fluorophore, or deposition of a fluorescent microparticle or nanoparticle. Fluorophores can be attached via a variety of chemical means known to the art, including coupling of fluorophore-labeled phosphoramidites to surface-attached alcohols, coupling of fluorophore-N-hydroxylsuccinimide esters to surface-bound primary amines, coupling of fluorophore acid chlorides-to either surface bound alcohols or surface-bound primary amines or coupling of fuorophore maleimide esters to surface-bound sulfhydryl groups. Fluorophores may also be deposited, after absorption by or conjugation to a carrier matrix that strongly and-irreversibly binds to the microarray support (e.g., polylysine). Finally, fluorophore-labeled microparticles (e.g., latex microspheres) or nanoparticles (e.g. fluorescent semiconductor nanocrystals) may be deposited on the surface. Adhesion may be achieved via surface forces, chemical conjugation or chemical adhesives (i.e., glue). In all cases, the amount of fluorophore attached can be controlled by coupling or depositing a mixture of fluorophore and a similar non-fluorescent molecule or particle, keeping the total concentration (fluorescent plus non-fluorescent) constant.

The array 12 may cover an area of less than 100 $cm^2$, or even less than 50, 10 or 1 $cm^2$. In many embodiments, substrate 10 will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm.

Usually, borders "B" around scan region 8 less than about 5–15 mm are provided. It is often desirable to lay down features as close to the edge of the substrate as possible so as to maximize the number of different probes that may be displayed on a given surface area. As such, in many array configurations, the width of a border, if present, does not exceed about 20 mm, usually does not exceed about 10 mm and more usually does not exceed about 5 mm.

An array identifier 40 in the form of a bar code in FIG. 1, is preferably associated with the array 12, by being provided on the same substrate 10 adjacent one of the arrays 12. In the case where more than one array 12 is present on the same substrate 10, a separate identifier can be provided adjacent each corresponding array 12 if desired. Identifier 40 may either contain information on the layout of array 12 or be linkable to a file containing such information in a manner such as described in U.S. Pat. No. 6,180,351. Each identifier 40 for different arrays may be unique so that a given identifier will likely only correspond to one array 12 or to a plurality of arrays 12 on a given substrate 10. This configuration can be accomplished by making identifier 40 sufficiently long and incrementing or otherwise varying it for different arrays 12 or arrays 12 on the same substrate 10, or even by selecting it to be globally unique in a manner in which globally unique identifiers are selected as described in U.S. Pat. No. 6,180,351.

Arrays such as those of FIGS. 1–3 can be fabricated using drop deposition from pulse-jets of either polynucleotide precursor units (such as monomers) in the case of in situ fabrication, or a previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren, et al., and the references cited therein. Other drop deposition methods can be used for fabrication, as well. Also, instead of drop deposition methods, other array fabrication method may be used including pin spotting and the techniques described in U.S. Pat. Nos. 5,599,695, 5,753,788, and 6,329,143.

Inter-feature areas 13 need not be present particularly when the arrays are made by light directed methods as described in those patents. In use, a feature can detect a polynucleotide of a complementary sequence by hybridizing to it, such as polynucleotide 18 being detected by feature 16a in FIG. 3 (the "*" on polynucleotide 18 indicating a label such as a fluorescent label). Use of arrays to detect particular moieties in a sample (such as target sequences) are well known. The layer thickness of the probes at features 16, together with any detected target to which they are bound, is often less than 500 nm thick, and often less than 200, 100, 50 or 20 nm in thickness.

Figure 4:
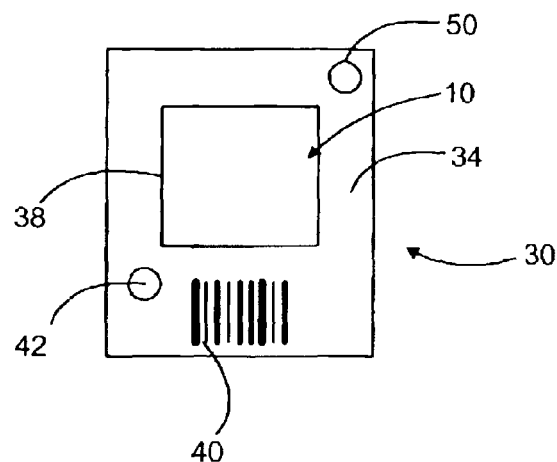
FIG. 4 is a front view of another array package in the form of a cartridge, which may be used in the present invention.

Referring now to FIG. 4 an array package 30 may include a housing 34 that has received substrate 10 adjacent an opening. Substrate 10 is sealed (such as by the use of a suitable adhesive) to housing 34 around a margin 38 with the second surface 11b facing outward. Housing 34 is configured such that housing 34 and substrate 10, define a chamber into which features 16 of array 12 face. This chamber is accessible through resilient septa 42, 50 which define normally closed ports of the chamber. In this case, array package 30 may be associated with the identifier 40 by providing identifier 40 on housing 34. Such association of any these or other items with the array, can be accomplished, for example, by the items being present in the same package as the array when shipped to an end user.

The components of the embodiments of either array package 30 described above, may be made of any suitable material. For example, housing 34 can be made of metal or plastic such as polypropylene, polyethylene or acrylonitrile-butadiene-styrene ("ABS"). Substrate 10 may be of any suitable material, and is preferably sufficiently transparent to the wavelength of an interrogating and array emitted light, as to allow interrogation from its underside whether situated in a housing 34 or not. Such transparent and non-transparent materials include, for flexible substrates: nylon, both modified and unmodified, nitrocellulose, polypropylene, and the like. For rigid substrates, specific materials of interest include: glass; fused silica, silicon, plastics (e.g., polytetrafluoroethylene, polypropylene, polystyrene, polycarbonate, and blends thereof, and the like); metals (e.g., gold, platinum, and the like).

The first surface 11a of substrate 10 may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated). The materials from which substrate 10 and housing 34 (at least the portion facing toward the inside of chamber 36) may be fabricated should ideally themselves exhibit a low level of binding during hybridization or other events.

Figure 5:
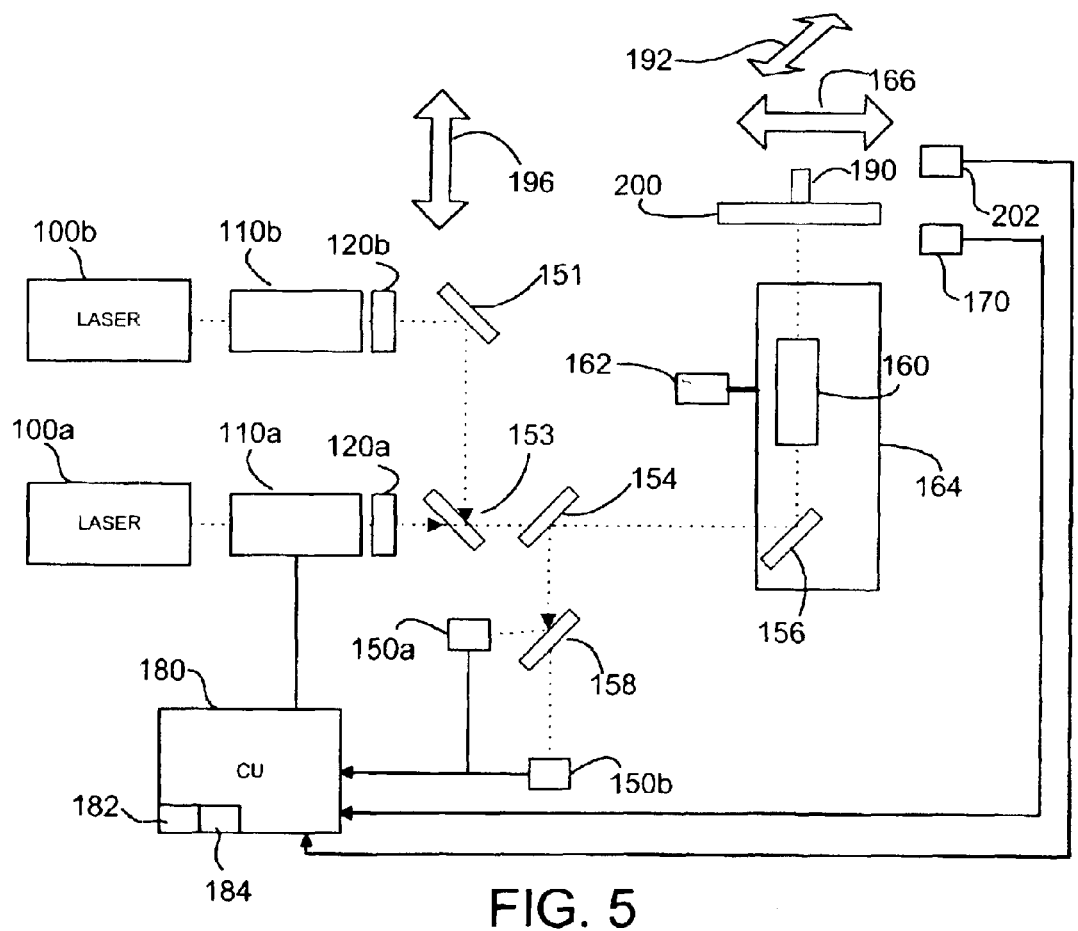
FIG. 5 schematically illustrates an apparatus as may be used in the present invention.

Referring now to FIG. 5, an apparatus of the present invention (which may be generally referenced as an array "scanner") is illustrated. A light system provides light from a laser 100 that passes through an electro-optic modulator (EOM) 110 with attached polarizer 120. Each laser 100a, 100b may be of different wavelength (e.g., one providing red light and the other green) and each has its own corresponding EOM 110a, 110b and polarizer 120a, 120b. The beams may be combined along a path toward a holder or caddy 200 by the use of full mirror 151 and dichroic mirror 153. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include, a suitably programmed processor. Thus, each EOM 110 and corresponding polarizer 120 together act as a variable optical attenuator which can alter the power of an interrogating light spot exiting from the attenuator. The remainder of the light from both lasers 100a, 100b is transmitted through a dichroic beam splitter 154, reflected off fully reflecting mirror 156 and focused onto either an array 12 of an array package 30 mounted on holder 200, or a calibration member 230, whichever is at a reading position, using optical components in beam focuser 160. Light emitted (in particular, fluorescence) at two different wavelengths (e.g., green and red light) from features 16, in response to the interrogating light, is imaged using the same optics in focuser/scanner 160, and is reflected off mirrors 156 and 154. The two different wavelengths are separated by a further dichroic mirror 158 and are passed to respective detectors 150a and 150b.

More optical components (not shown) may be used between the dichroic and each detector 150a, 150b (such as lenses, pinholes, filters, fibers, etc.) and each detector 150a, 150b may be of various different types (e.g., a photo-multiplier tube (PMT) or a CCD or an avalanche photodiode (APD)). All of the optical components through which light emitted from an array 12 or calibration member 230 in response to the illuminating laser light, passes to detectors 150a, 150b, together with those detectors, form a detection system. This detection system has a fixed focal plane. A scan system causes the illuminating region in the form of a light spot from each laser 100a, 100b, and a detecting region of each detector 150a, 150b (which detecting region will form a pixel in the detected image), to be scanned across multiple regions of an array or array package 30 mounted on holder 200. The scanned regions for an array 12 will include at least the multiple features 16 of the array. In particular the scanning system is typically a line by line scanner, scanning the interrogating light in a line across an array 12 when at the reading position, in a direction of arrow 166, then moving ("transitioning") the interrogating light in a direction into/out of the paper as viewed in FIG. 5 to a position at an end of a next line, and repeating the line scanning and transitioning until the entire array 12 has been scanned.

This scanning feature is accomplished by providing a housing 164 containing mirror 158 and focuser 160, which housing 164 can be moved along a line of pixels (i.e., from left to right or the reverse as viewed in FIG. 5) by a transporter 162. The second direction 192 of scanning (line transitioning) can be provided by second transporter which may include a motor and belt (not shown) to move caddy 200 along one or more tracks. The second transporter may use the same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The reader of FIG. 5 may further include a reader (not shown) that reads an identifier 40 from an array package 30. When identifier 40 is in the form of a bar code, that reader may be a suitable bar code reader.

Of course, the movements 166 and 192 may be accomplished by actuating holder 200 or housing 164 alone. Still further, the movement roles described for each element above may be swapped.

An autofocus detector 170 is provided to sense any offset (variation in slope) between different regions of array 12 when in the reading position, and a determined position of the focal plane of the detection system. The autofocus system includes detector 170, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, a second position detector 202, also feeding back to the CU, preferably measures the absolute position (i.e., relative to the apparatus) of the servo-controlled adjuster 190). As above with respect to movements 166 and 192, it should be observed that focus servo control movement 196 may occur in connection with housing 164 instead of the holder. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors. In addition, details regarding maintaining or setting lens focus upon changing direction may be appreciated in U.S. Patent Application Attorney Docket No.10020373-1, entitled "Bi-Directional Scanner Control System," filed Feb. 28, 2001 which provides algorithms to account for variability in assay slide slope.

In any case, array orientation and configuration is of little consequence since focus can be set to features 16 either directly, or looking through a transparent substrate medium if the array is inverted for scanning (for instance, when upper surface 11a is blocked-off with housing features and surface 11b is exposed).

Controller 180 of the apparatus is connected to receive signals from detectors 150a, 150b, these different signals corresponding to different "channels", i.e. signals which results at each of the multiple detected wavelengths from emitted light for each scanned region of array 12 when at the reading position mounted in holder 200. Controller 180 also receives the signal from autofocus offset detector 170 and absolute servo position detector 202, and provides the control signal to EOM 110, and controls the scan system. Controller 180 may also analyze, store, and/or output data relating to emitted signals-received from detectors 150a, 150b in a known manner.

Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40).

Controller 180 is suitably programmed to execute all of the steps required by it during operation of the apparatus, as discussed further below. Alternatively, controller 180 may be any hardware or hardware/software combination which can execute those steps.

In one mode of operation, the array in package 30 is typically first exposed to a liquid sample. This liquid sample may be placed directly on substrate 10 or introduced into a chamber through one of the septa 42, 50. The array may then be washed and scanned with a liquid (such as a buffer solution) present in the chamber and in contact with the array, or it may be dried following washing. After mounting a given array package 30 in cradle 200 (either with the array features on the glass surface nearer to, or further from, the lens—depending, at least, upon the lens setup) the identifier reader may automatically (or upon operator command) read array ID 40, and use this to retrieve information on the array layout. Such information may be retrieved directly from the contents of identifier 40 when ID 40 contains such information. Alternatively, identifier 40 may be used to retrieve such information from a database containing the identifier in association with such information. Such a database may be a local database accessible by controller 180 (such as may be contained in a portable storage medium in drive 182 which is associated with package 30, such as by physical association with package 30 when received by the user, or by a suitable identification), or may be a remote database accessible by controller 180 through communication module 184 and a suitable communication channel.

The saved results from a sample exposed array, read by the scanner set according to the methodology described in detail below, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

Substrate 10 may actually carry more than one array 12, arranged as desired. While the substrate shown is planar and rectangular in form, other shapes may also be used—with optional housing 34 being adjusted accordingly. Still, in many embodiments, substrate 10 will be shaped generally as a planar, rectangular solid, having a length in the range about 4 mm to 200 mm, usually about 12 mm to 150 mm, more usually about 20 mm to 80 mm; a width in the range about 4 mm to 200 mm, usually about 10 mm to 80 mm and more usually about 10 mm to 30 mm; and a thickness in the range about 0.01 mm to 5.0 mm, usually from about 0.1 mm to 2 mm and more usually from about 0.9 to 1.2 mm. However, larger substrates can be used. Additionally, during scanning it is possible to illuminate all pixels of a line simultaneously (for example, by using a line of light emitting diodes).

Methodology

With controls features as described above, certain approaches and variations employing the controls for setting a scanner system as described or another suitable scanner are described in connection with FIGS. 6A–7B. FIG. 8 includes additional optional methodology that may be employed in connection with the present invention, as does that presented in U.S. Patent Application Atty. Docket No. 10011208-1, entitled "Maximum Sensitivity Optical Scanning System," filed Feb. 28, 2002, incorporated herein by reference.

The methodology in FIG. 8 involves an array scan 200. The array scan may include scanning each channel to be scanned or the scanning process may be conducted in a serial fashion. In either case, scan results are processed using software such as GenePix by Axon Instruments, QuantArray by Perkin Elmer or Feature Extraction by Agilent of Palo Alto, Calif. and these results are checked for saturation in check 202.

If there are saturated results, scanner settings are adjusted downward in adjustment step 204. The amount that system settings are turned down may be a function of some average signal level of the features. For instance, if a majority of features are saturated a decrease factor of 90% may be appropriate, whereas if about half the features are saturated, then a decrease by 50% may be used, etc. If there are no saturated results, upward adjustment of the scanner system occurs as indicated in adjustment step 206. As with downward adjustment, upward adjustment may be attempted in a manner tied to the actual data produced. Any number or variety of estimation routines may be applied for either type of adjustment.

In addition, upward and/or downward system setting adjustment may be accomplished through various manipulations of the scanner system hardware. This is true for any adjustment method described herein. Either one or both of the gain of the excitation light source(s) or detector(s) (e.g., PMT, CCD, etc.) may be changed to produce a reduced or increased intensity scale factor. In the case of altering PMT sensitivity, where the relation between applied voltage and gain is non-linear, the extent of change may be predicted utilizing the power law published by hardware vendors with empirically determined coefficients to make an estimate or by an iterative approach in testing gain obtained in varying voltage against expected results.

However adjustment is made, the methodology shown in FIG. 8 may terminate upon adjustment or involve another scan that repeats the check and adjustment process actions. In either case, this methodology is typically used as a precedent step to the other methods described below, taken to gather data for basic scanner system settings, especially initial PMT settings.

Turning now to FIG. 6A, methodology centered on the control features of the invention is disclosed. As described above, the process starts with an array scan 208. This scan may include reading each channel to be compared. Scan step 208 is followed by a ratio check step 210 in which it is determined whether control feature intensities correspond or substantially correspond to the expected ratio (usually, 1:1 in terms of image intensity). If the resultant ratio matches (or substantially matches) the expected value, then the process end, with the full results of scanning the array being treated as acceptable. Alternately, system settings are adjusted so a subsequent scan should produce the expected ratios (usually, equalizing the ratio). After such action, another scan step 214 may be engaged followed by the end of the process or scan step. 208 may be repeated to be followed by a subsequent check 210 and so forth.

Figure 6:
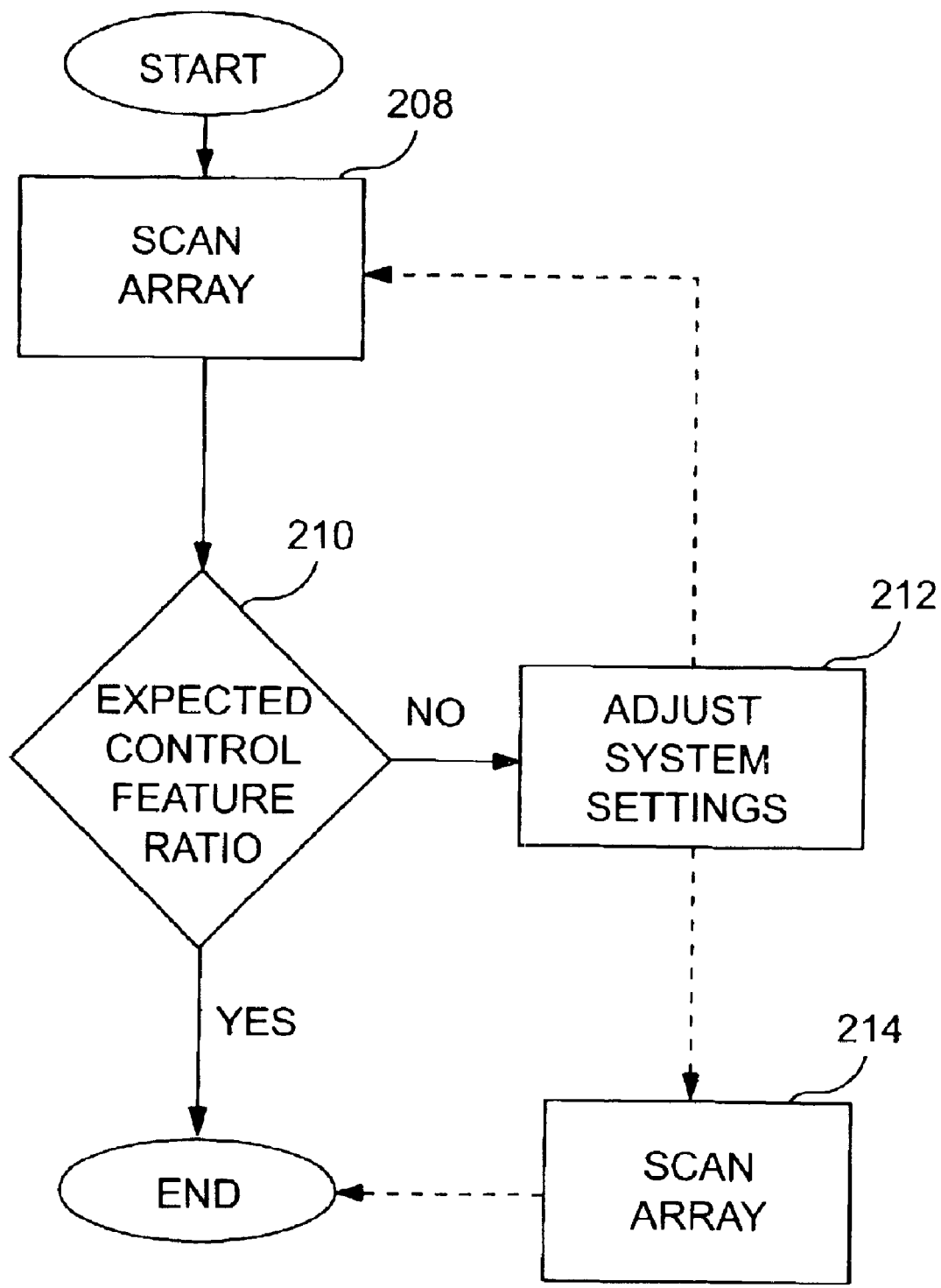
FIGS. 6A and 6B are flow charts showing control-based scanner tuning approaches considering control feature ratios.
Figure 6B:
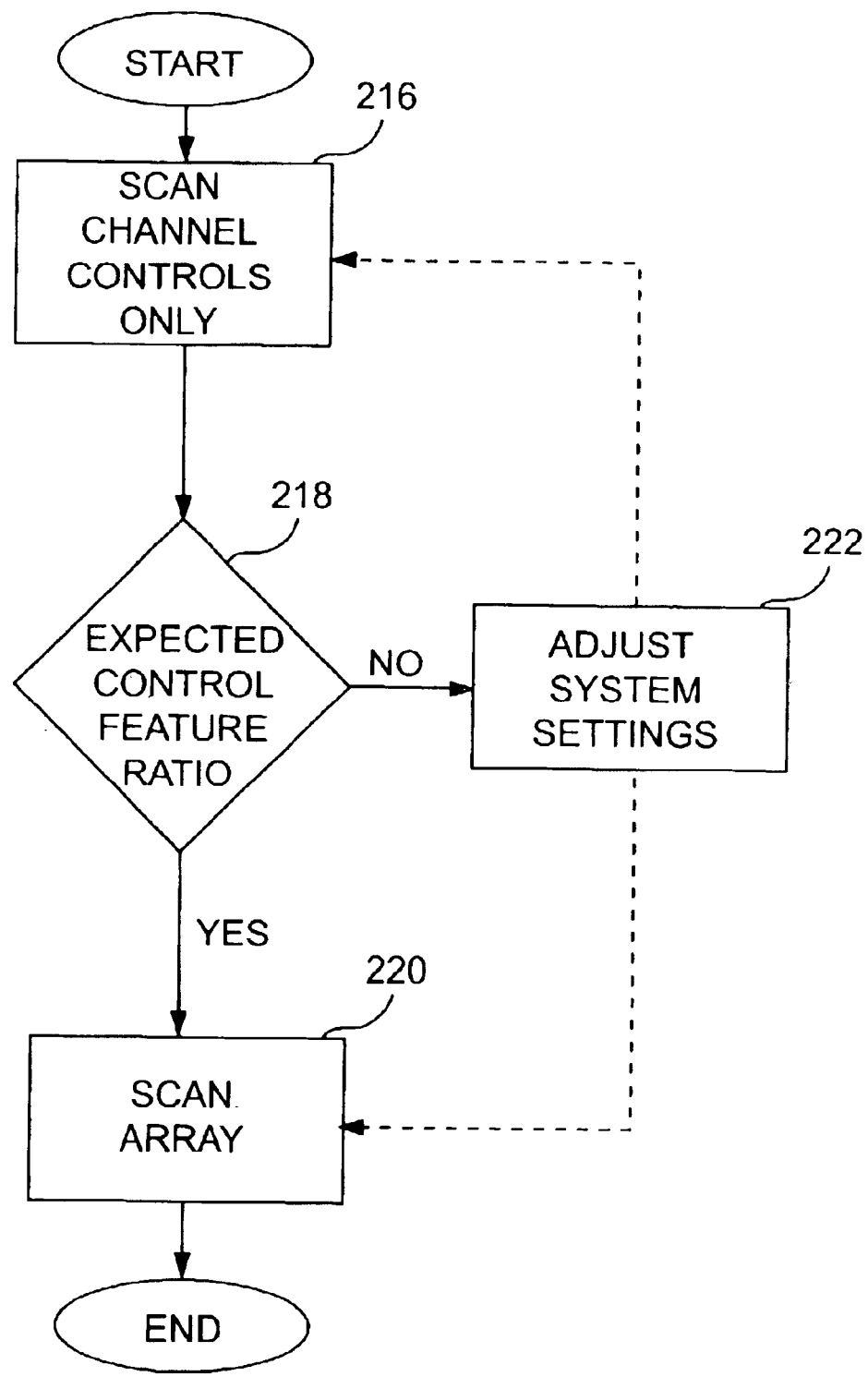

Another approach to adjusting system setting in view of an expected color intensity ratio is shown in FIG. 6B. In contrast the approach taken in FIG. 6A, the first scan 216 of this portion of the process only involves the control features. This helps avoid photobleaching of other array features. Upon running check 218 to determine if the control results match the expected ratio, a complete scan 220 of the array will follow if the ratios match (or substantially match). If not, a scanner adjustment step 222 follows. In which case, another control feature scan 216 may proceed and be checked, followed by such optional activity as shown.

Where more than one control feature with different intensities—under selected circumstances—is provided for each channel, the processes shown in FIGS. 6A and 6B may be run for each of the control features for a given pair (or set) of colors.

Similar feature-by-feature methodology may be taken in running through the processes shown in FIGS. 7A and 7B, and 9A–9B as well. The approach in the "B" figures may generally be preferred over those in the "A" figures due to the relative protection each scheme provides from photobleaching relative to the other processes.

Figure 7A:
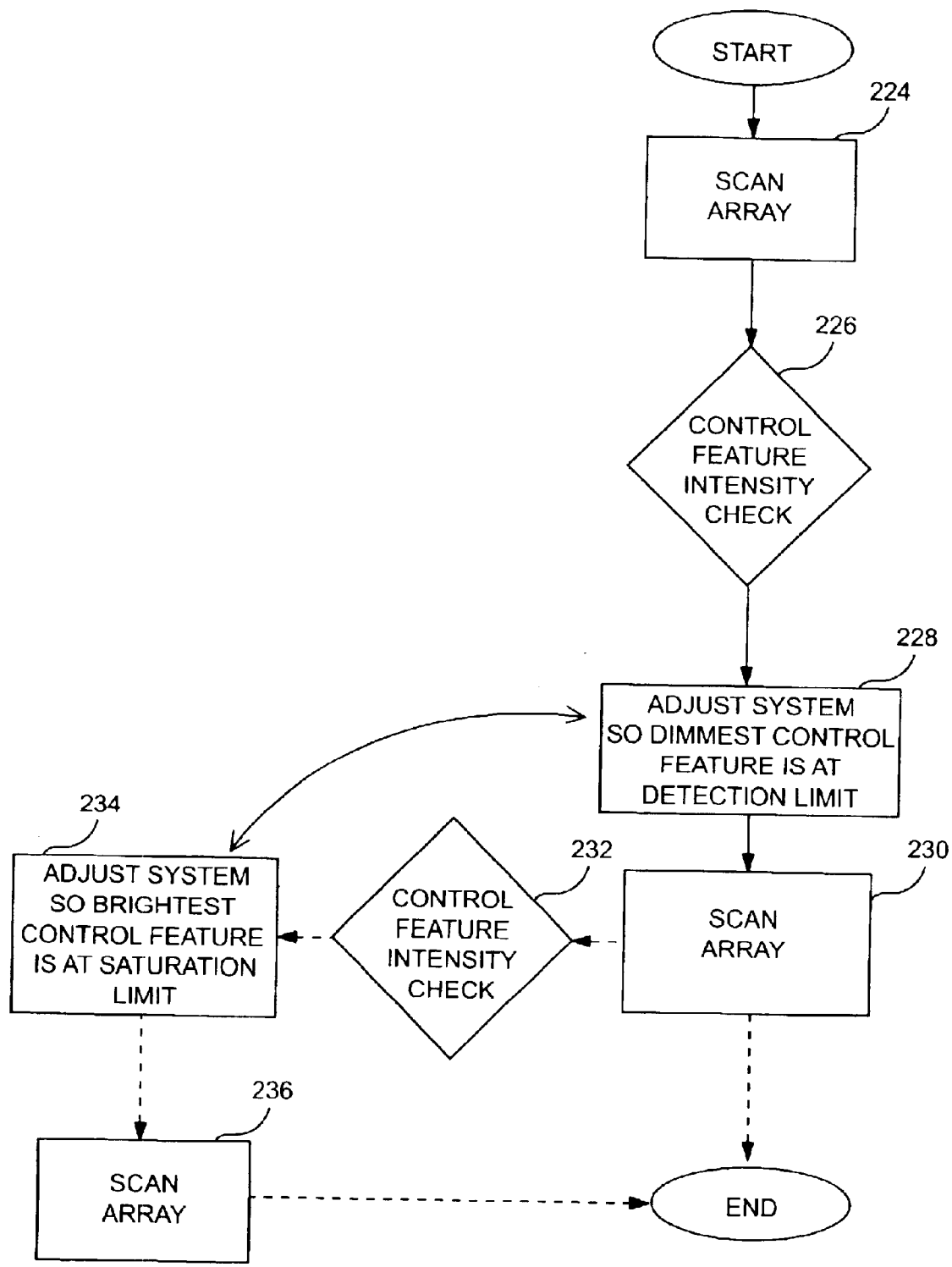
FIGS. 7A and 7B are flow charts showing alternate control-based scanner tuning approaches considering control feature intensity relative to detection and saturation limits.
Figure 8:
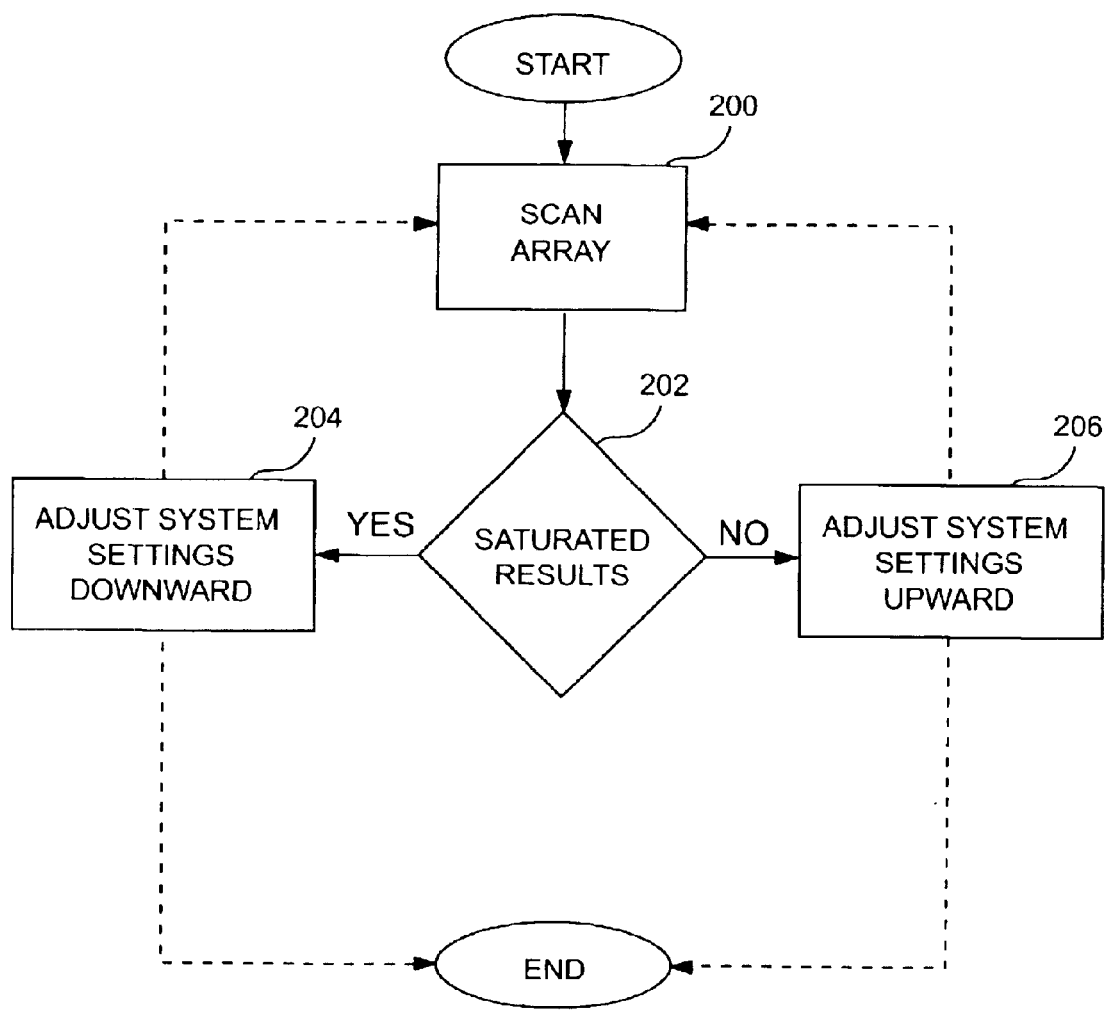
FIG. 8 is a flow chart showing an optional and initial scanner setup approach.

Regarding the approach taught in FIG. 7A, it also generally begins with an array scan or act 224. This is followed by a control feature intensity check 226. Next, the lower end of detection resolution is adjusted so that the dimmest control feature(s) on the array are at the lower detection limit of the instrument, or a fixed amount above the detection limit (e.g., within about 10%, about 5%, about 2.5%, about 1% or even closer to the lowest limit of detection for the scanner). This adjustment step 228 may be followed by another array scan 230 at the new settings followed by another control feature intensity check 232. Based on this check, another scanner adjustment 234 is made so that the brightest control feature(s) are at the upper limit of system sensitivity/saturation limit of the system, or at a fixed fraction of the saturation limit (e.g., within about 10%, about 5% about 2.5%, about 1% or even closer to the saturation level for the scanner). When adjustment for scanner upper limits is carried out, a final scan 234 to retrieve fully calibrated data is generally taken. In instances where sequential adjustment is not made, scan 230 may be the final scan.

Figure 7B:
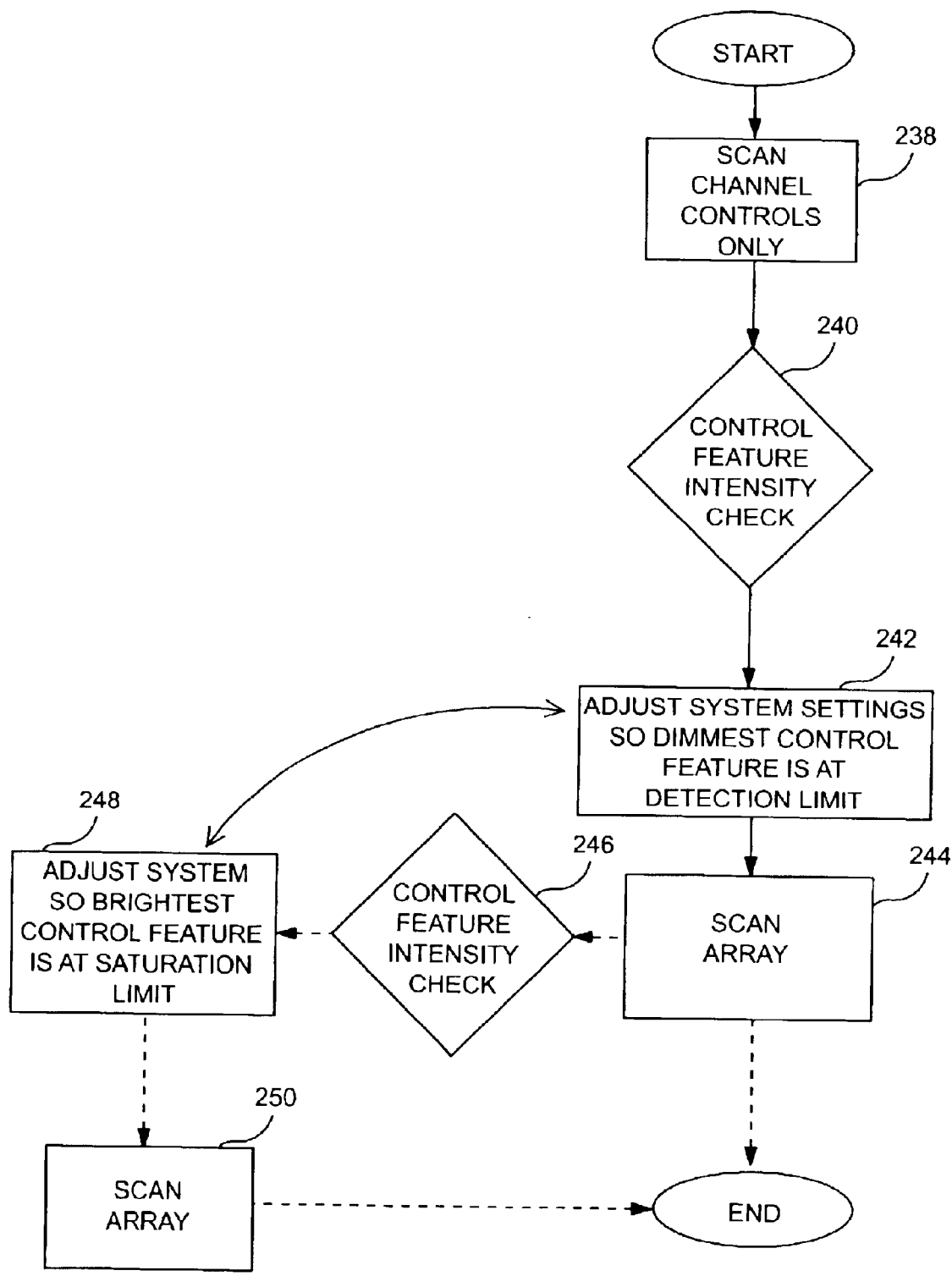

FIG. 7B depicts a related methodology to that shown in FIG. 7A. However, instead of making a full array scan 224 initially, a scan 238 for control features only is first employed. This scan if followed by checks 240 and/or 246 and adjustments 242 and/or 248. One or more full array scans 244 and/or 250 follow as shown. In any case, adjustment as described in connection with FIG. 7A is contemplated for approaches based on FIG. 7B as well.

It is also to be appreciated that the order of such sequential checking/tuning in the methods of FIGS. 7A and 7B may be altered or swapped as indicated by the double-headed arrows in the figures. Further, as in other variations of the invention, the steps may be taken sequentially for each channel/color and/or in a turn-based fashion a making scan, check and/or adjustment for each channel before moving on to the next act or step.

Figure 9:
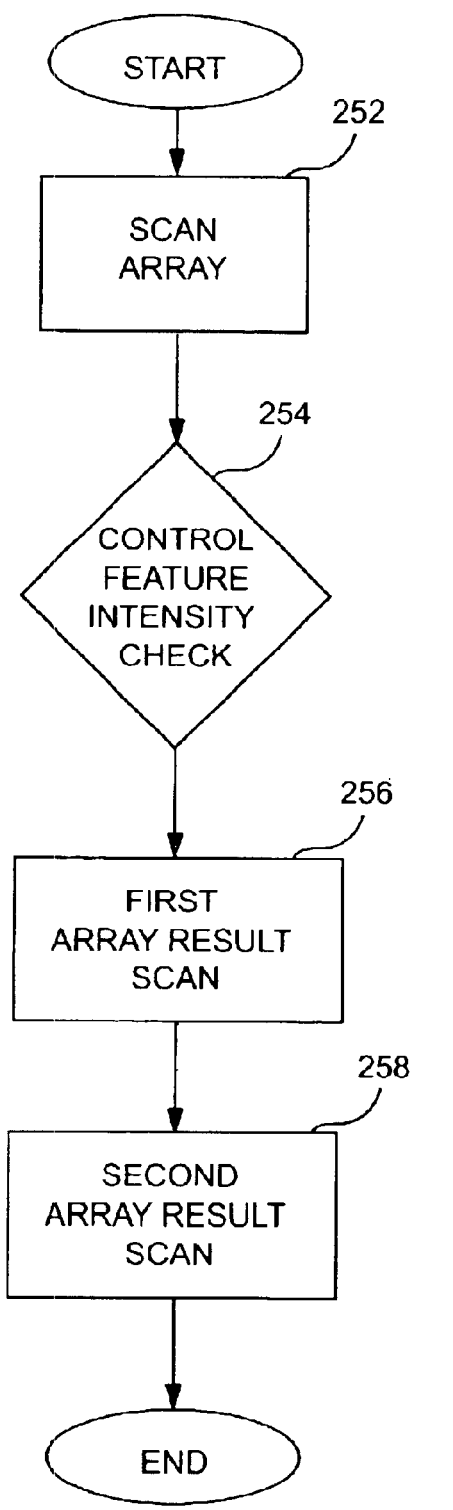
FIGS. 9A and 9B are flow charts showing additional scanner tuning approaches considering control feature intensity as applied to subsequent array scans.
Figure 9:
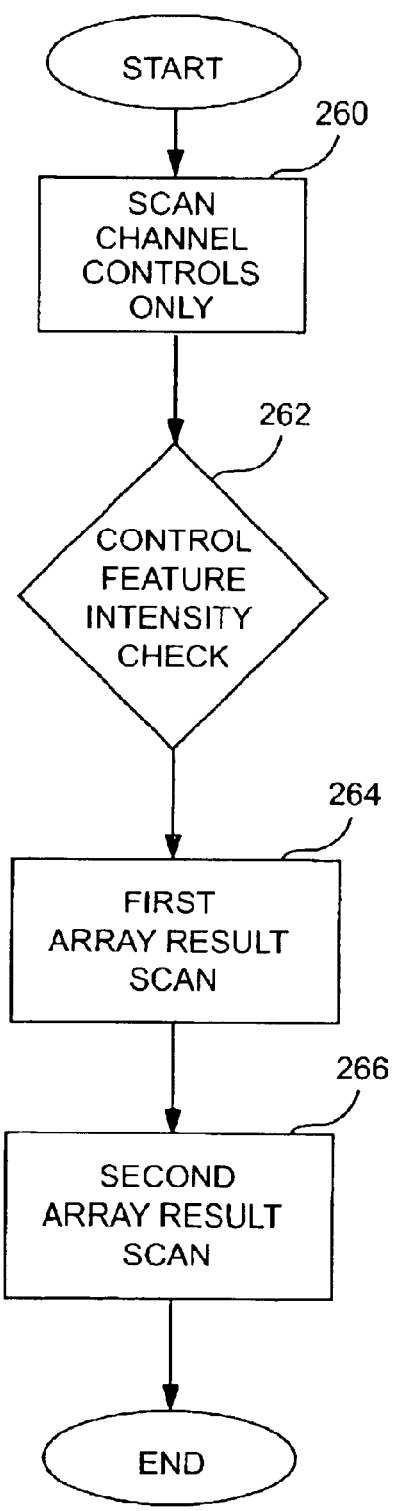

In the method shown in FIG. 9A, rather than performing multiple scans of control features (one to determine system settings for the low end of the dynamic range and one to determine system settings for the high end), an approach is shown in which only one test scan 252 is run. A check 254 accounts for the intensities of a number of control features.

By utilizing different intensity control features, a single scan of the features can provide data to determine appropriate PMT settings to 1) make the lowest level feature result(s) just above detection limit; 2) to make the highest level feature result(s) just below the detector upper limit/saturation level; and/or 3) make the dye ratios equal to the desired level(s)—usually, correcting the ratio of the channels to the expected ratio. After such a scan is run and such data as necessary is obtained, two scans 256, 258, respectively, are run with the PMT/scanner sensitivity settings thus determined. Both sets of scan results would, typically, be available to a user as well as any combined output utilizing the determined scale factors.

In FIG. 9B, a similar approach to that in FIG. 9A is shown except that scan 260 limited to the control features is directed. This action (preferably for each channel—though possibly for only one channel) is followed by a control feature intensity check 262 and subsequent full array scans 264 and 266. As with all other methods according to the present invention, each step or act depicted may be run sequentially for one channel and then another, etc. or be run back-to-back.

In yet another variation of the invention, multiple channel control features are utilized to account for system or dye non-linearites. "Self-quenching" dye interaction can produce such non-linearity. That is to say the amount of fluorescence emitted by the dye doesn't increase linearly with increases in dye amount. An instance in which this may occur is when dye molecules become so densely packed that they interact with one another. This interaction can change the excitation/emission spectra of the dye molecules altering total fluorescence (usually—a reduction, hence the term "quenching").

Such an approach would involve selecting scanner settings for one or more full scans of the array that best account for such system non-linearities. For instance, the measured ratio of channels could be different for different intensities of features. This could occur due to scanner non-linearities, or it could occur due to properties of the dye and/or array (e.g., self-quenching of dye). If this were the case, there would be different optimal PMT settings for different signal intensities. This cannot be compensated using post-scan processing of the data because the non-linearities will generally not have been measured. However, if optimal PMT settings are determined for a variety of feature intensities, the scanner can determine an optimal setting for the aggregate of these features. For instance, it could use the average ratio for all control features measured and then re-adjust to make this average ratio equal the expected level.

Figure 10A:
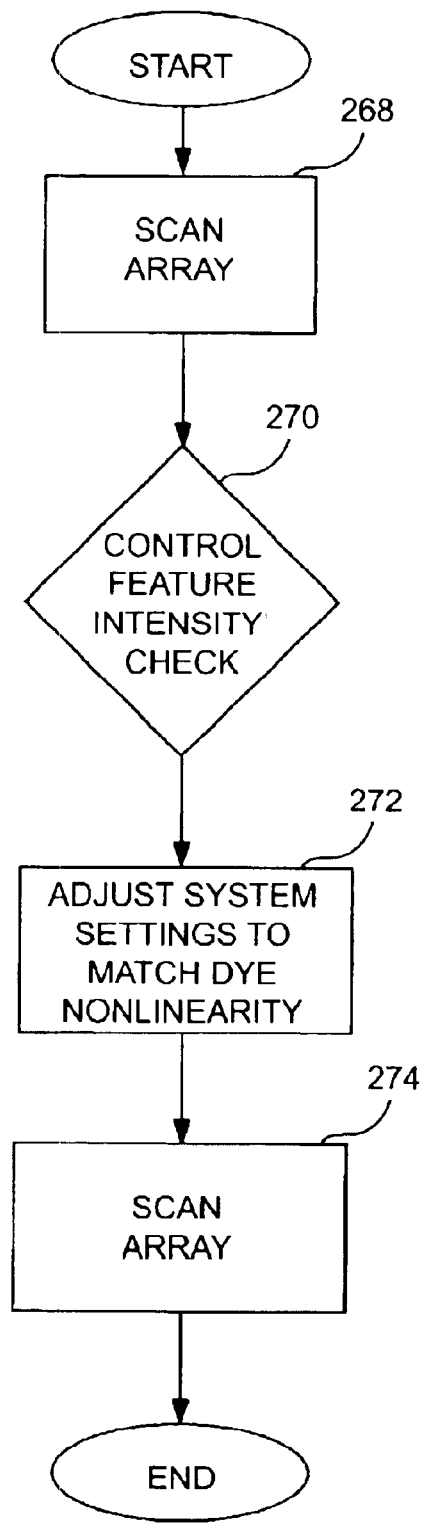
FIGS. 10A and 10B are flow charts showing further scanner tuning approaches considering control feature intensity to account for dye non-linearities.
Figure 10B:
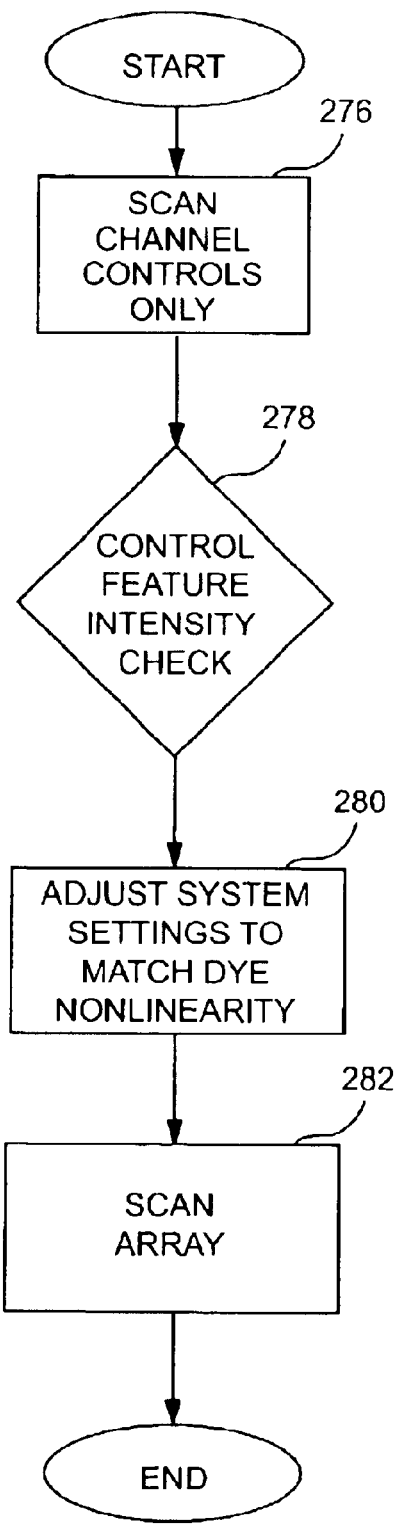

The manner in which the invention may be used in this regard is discussed with respect to FIGS. 10A and 10B. In FIG. 10A, a scan 268 is made of the array. This is followed by a check 270 of the intensity of a plurality (at least two) control features for a given channel. Next, a system adjustment 272 is made to pick optimal settings to account for any system non-linearites, including those presented by the dyes used or other factors. Then, an array scan 274 is carried out to obtain scan results. If this scan is performed with sensitivity settings for the two channels that sets the sensitivity ratio using the average of the various intensity control features, additional steps can be taken. Since the different intensity control features have been scanned, the relation between feature intensity and ratio of the different channels will be known. This relationship may be fit to a mathematical function and reported to the user along with the output file of the scan. At this point, the scan image (with the non-linearity information attached to the file) may be passed to feature extraction software. The feature extraction software may then compensate for the non-linearities observed. For example, for two-color scanning if at low intensities the red channel is relatively brighter than the green by 7% (and they are expected to be equal), then the feature extraction software would lower the red signal for such features by 7% before presenting the data back to the user.

FIG. 10B depicts an initial scan of the array as in FIG. 10A, except that this scan 276 only involves the plurality of array features set to have different intensities. Following this scan, a check 278 and an adjustment 280 in view of the intensities detected are made. A full scan 282 of the array follows.

Further variation of the invention is contemplated as well. Each of the methods in the figures has been indicated and, largely, discussed in the context of a discreet approach. However, it is specifically contemplated that one or more of the actions indicated in any one figure may be the same as that indicated in another, thereby linking the processes together or interrelating them. For example, the methods shown in FIGS. 6A and 7A may be combined such that array scan 208 and array scan 224 are one and the same. In which case, that scan is followed both by 1) a check 210 to determine if an expected control ration is present (to be followed by such action as may be further indicated to balance the channels) and 2) a control feature intensity check 226 (to be followed by such action as may be further indicated to maximize dynamic range).

It will readily be appreciated that other viable combinations of activities from each of the figures are possible. The activity of FIGS. 6B and 7B can be combined in like fashion to that in FIGS. 6A and 6B; scan 200 of FIG. 8 may, for example, may be the same scan as scan 208 or 224; etc. Combining such action can help avoid photobleaching. The motivation to do so would be reduced (or eliminated), however, with respect to methodology only employing a control feature scan 216 or 238, etc. first.

In any case, all such options or permutations as are consistent with one another are considered to be within the scope of the invention. The different numerals applied in the discussion of various methods have simply been applied for the sake of convenience as references for the discussion above.

Regardless of the particular manner in which the methods are run, they present additional utility to that which has been specifically described above. Namely, the methods shown, particularly routines involving those shown in FIGS. 6A–7B, may be run on arrays to determine if they are functioning properly and or manufactured to acceptable standards. By using a system known to be calibrated, for instance with an array known to be of acceptable quality, variances reported in results obtained at the "check" steps (210/218/226/232/240 /246/254/262/270/278) may be recorded and subsequently reported to a manufacture, quality control expert, etc. for use in validating and or improving, rating and/or adjusting array manufacture. In these variations of the invention, array scans for experimental data acquisition (214/220/230/236 /244/250/256/258/ 264/266/276/274/284/282) may be omitted as unnecessary. Also, the data may be used to confirm the performance and repeatability of the hybridization process.

Array Use

The subject methods and systems find use in a variety of different applications, where such applications are generally arrays based analyte detection applications in which the presence of a particular analyte in a given sample is detected at least qualitatively, if not quantitatively, using an array based protocol. Protocols for carrying out such assays are well known to those of skill in the art and need not be described in great detail here. Generally, the sample suspected of comprising the analyte of interest is contacted with an array under conditions appropriate for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which nucleic acid arrays are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced include: gene discovery assays, differential gene expression analysis assays; nucleic acid sequencing assays, and the like. U.S. patent Nos. describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in: U.S. Pat. Nos. 4,591,570; 5,171,695; 5,436, 170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

As noted above, in certain embodiments, the subject methods include a step of transmitting data from at least one of the detecting and deriving steps, as described above; to a remote location. The data may be transmitted to the remote location for further evaluation and/or use. Any convenient telecommunications means may be employed for transmitting the data, (e.g., facsimile, modem, internet, etc.)

As such, the array will typically be exposed to a sample (e.g., a fluorescently labeled analyte such as a protein containing sample) and the array then read according to the methodology described above. A scanner may be used for this purpose which is similar to the AGILENT MICROARRAY SCANNER available from Agilent Technologies, Palo Alto, Calif. Other suitable apparatus and methods are described in U.S. patent application Ser. Nos. 09/846,125 entitled, "Reading Multi-Featured Arrays," by Dorsel, et al.; and Ser. No. 09/430,214 entitled, "Interrogating Multi-Featured Arrays," by Dorsel, et al. As previously mentioned, these references are incorporated herein by reference as are all other references cited herein.

Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample or whether an organism from which a sample was obtained exhibits a particular condition). The results of the reading (processed or not) may be forwarded (such as by communication) to a remote location if desired, and received there for further use (such as further processing).

Though the invention has been described in reference to certain examples, optionally incorporating various features, the invention is not to be limited to the set-ups described. The invention is not limited to the uses noted or by way of the exemplary description provided herein. It is to be understood that the breadth of the present invention is to be limited only by the literal or equitable scope of the following claims. That being said,

We claim:

1. A method of reading an array having both control features and test features, said method comprising:

emplploying an array scanner to scan at least the control features to obtain control feature signal levels for a first channel and a second channel;

comprising said control feature signal levels for said first channel to control feature signal levels of said second channel;

wherein at least one ratio of the control feature signal levels from different channel is compared to an expected signal ratio from the different channels;

adjusting sensitivity of the scanner in view of the relative control feature signal levels for said first channel and said second channel; and scanning at least the test features.

2. The method of claim 1, wherein the adjustment made provides for the ratios of the signal levels to be substantially the same.

3. The method of claim 1, wherein the scanner is an optical scanner, the scanning assembly is a lens assembly, the control features are color control features, and the channels are different color channels.

4. The method of claim 1, wherein scanner system sensitivity is adjusted by adjusting a gain of one or more detectors.

5. The method of claim 1, wherein scanner sensitivity is adjusted so that the strongest signal level from any scanned control feature will be within 5% of a detector saturation.

6. The method of claim 1, wherein scanner sensitivity is adjusted so that the lowest signal level from any control features will be within 5% of a lowest limit of detection of a detector.

7. The method of claim 1, wherein the control features signal levels are utilized to compensate for non-linearity of at least one array scan in a manner selected from adjusting scanner sensitivity prior to al least one scan of the test features, and applying a relationship to results of at least one scan of the test features, wherein the relationship is a function of the control feature signal levels.

8. The method of claim 1, wherein the control features signal levels are utilized to scale results from a first, high-sensitivity scan and a second, low sensitivity scan.

9. The method of claim 1, wherein the control features and array test features are scanned before the adjustment.

10. The method of claim 1, carried out on a biopolymer array.

11. The method of claim 10, wherein said biopolymer is selected from the group consisting of polypeptides and nucleic acids.

12. The method of claim 1, further comprising transmitting a result from a reading of the array from a first location to a second location.

13. The method of claim 12, where said said location is a remote location.

14. A system programmed to operate according to the method of claim 1.

* * * * *

UNITED STATES PATENT AND TRADEMARK OFFICE
CERTIFICATE OF CORRECTION

PATENT NO.        : 7,089,123 B2
APPLICATION NO. : 10/261563
DATED             : August 8, 2006
INVENTOR(S)       : Corson et al.

It is certified that error appears in the above-identified patent and that said Letters Patent is hereby corrected as shown below:

On the Title page , in item (73), in "Assignee", in column 1, line 1, delete "Inc." and insert -- Inc., --, therefor.

On the Title page, in item (56), under "U.S. Patent Documents", in column 2, line 5, after "6/1998" delete "Sadlere et al." and insert -- Sadler et al. --, therefor.

On the Title page, in item (56), under "Other Publications", in column 2, line 1, delete "Scnner" and insert -- Scanner --, therefor.

On the Title page, in item (56), under "Other Publications", in column 2, line 2, delete "UserM anuel," and insert -- User Manual, --, therefor.

On the Title page, item (56), under "Other Publications", in column 2, line 2, delete "Technologies,M ay" and insert -- Technologies, May --, therefor.

On the Title page, in item (56), under "U.S. Patent Documents", in column 2, line 6, after "6,078,390 A" insert -- * --.

On the Title page, in item (56), under "U.S. Patent Documents", in column 2, line 6, after "Bengtsson" insert -- 356/318 --.

On the Title page, in item (56), under "U.S. Patent Documents", in column 2, line 12, after "6,371,370" delete "B1" and insert -- B2 --, therefor.

Column 19, line 42, in Claim 1, delete "emplploying" and insert -- employing --, therefor.

Column 19, line 45, in Claim 1, delete "comprising" and insert -- comparing --, therefor.

Column 20, line 27, in Claim 7, after "prior to" delete "al" and insert -- at --, therefor.

Column 20, line 37, in Claim 10, after "claim 1" delete ",".

UNITED STATES PATENT AND TRADEMARK OFFICE
CERTIFICATE OF CORRECTION

PATENT NO. : 7,089,123 B2
APPLICATION NO. : 10/261563
DATED : August 8, 2006
INVENTOR(S) : Corson et al.

It is certified that error appears in the above-identified patent and that said Letters Patent is hereby corrected as shown below:

Column 20, line 45, in Claim 13, delete "said said" and insert -- said second --, therefor.

Signed and Sealed this

Ninth Day of January, 2007

JON W. DUDAS
*Director of the United States Patent and Trademark Office*